United States Patent [19]

Bryan

[11] Patent Number: 5,306,275
[45] Date of Patent: Apr. 26, 1994

[54] LUMBAR SPINE FIXATION APPARATUS AND METHOD

[76] Inventor: Donald W. Bryan, 6151 S. Woodland Dr., Ogden, Utah 84403

[21] Appl. No.: 999,005

[22] Filed: Dec. 31, 1992

[51] Int. Cl.$^5$ ............................................... A61F 5/02
[52] U.S. Cl. ........................................ 606/61; 606/60; 606/65; 606/66; 606/72; 606/73; 606/86
[58] Field of Search ................ 606/53, 60, 61, 65, 606/66, 72, 73, 86, 87, 103

[56] References Cited

U.S. PATENT DOCUMENTS

| | | | |
|---|---|---|---|
| 4,887,595 | 12/1989 | Heinig et al. | 606/73 |
| 4,920,959 | 5/1990 | Witzel et al. | 606/53 |
| 5,030,220 | 7/1991 | Howland | 606/61 |
| 5,122,131 | 6/1992 | Tsou | 606/53 |
| 5,154,719 | 10/1992 | Cotrel | 606/72 |
| 5,190,543 | 3/1993 | Schläpfer | 606/72 |
| 5,217,497 | 6/1993 | Mehdian | 606/61 |
| 5,219,349 | 6/1993 | Krag et al. | 606/53 |
| 5,242,445 | 9/1993 | Ashman | 606/73 |

Primary Examiner—Stephen C. Pellegrino
Assistant Examiner—J. A. Schmidt
Attorney, Agent, or Firm—J. Winslow Young

[57] ABSTRACT

A spinal fixation apparatus and method wherein various elements are mounted to the vertebra and the sacrum of a spine and are selectively interconnected to achieve a predetermined fixation and/or correction of a particular spinal condition. The apparatus includes pedicle screws, bone screws, sacral rods, sublaminar hooks, spinous process hooks, longitudinal rods, lateral rods, universal interlinks, rod clamps, and pedicle screw anchors, all of which can be readily interconnected into a predetermined construct as a spinal fixation apparatus. A burr guide apparatus is provided to prepare the access site for a pedicle screw and a sacral screw guide is used to accurately align the pilot holes for the sacral screws.

27 Claims, 14 Drawing Sheets

LUMBAR SPINE FIXATION APPARATUS AND METHOD

BACKGROUND

1. Field of the Invention

This invention relates to instrumentation for achieving spinal fusion and, more particularly, to a spinal fixation apparatus and method for fixation of the lumbar spine and the lumbosacral spine to aid the fusion of these regions of the spine.

2. The Prior Art

The spine is a flexible, multisegmented column that serves to maintain the upright posture while providing mobility to the axial skeleton. The spine also protects the delicate neural structures of the spinal canal. In fulfilling these functions, the spine can be subjected to large forces. These large forces are assumed to play a dominant role in the etiology of low back pain. Excessive forces on the spine can also produce life-threatening traumatic injuries and may contribute to an increased rate of degenerative change.

The lumbar spine serves two basic functions. It encases and protects vital neural elements and provides structural support for the body by transmitting the weight of the body through the pelvis to the lower extremities. Since there are no ribs attached to it, the lumbar spine has a relatively wide range of motion.

The back is made up of bone, intervertebral discs, synovial joints with their articular cartilage, synovial capsules and supporting ligaments, muscle, fascia, blood vessels, nerves, and skin. As in other areas of the body, these elements are subject to a variety of pathological disturbances: inflammation, trauma, neoplasm, congenital anomalies, etc. Trauma frequently results in damage at the upper end of the lumbar spine, where the mobile lumbar segments join the less mobile dorsal spine. Degenerative changes tend to develop in the lower lumbar intervertebral discs, most commonly in the third decade. Osteoarthritis produces changes in the facet joints by middle age. Pain in the low back is a complaint of about 80% of the members of the human race at some period of life and is responsible for a large percentage of patient visits to physicians.

One of the methods used to treat disabling pain and neurological compromise produced by any of the above noted pathological conditions has been spinal fusion. Spinal fusion has been a controversial topic since the first procedures were performed in the early nineteen hundreds. Indications and techniques were argued then and continue to be a constant source of lively discussion in the orthopedic literature. It is also interesting to note that the development of spinal fusion techniques predates the understanding and surgical treatment of lumbar disc disease. It is the intersection and intermingling of indications for these two procedures, disc excision and lumbosacral fusion, that have produced the most controversy.

The earliest spinal fusion techniques were basically posterior interlaminar fusions. Subsequently, a few years of experience with these techniques led to the evolution of posterolateral techniques allowing a larger area for bone grafting and fusion. However, as orthopedists recognized the relatively high rate of unsatisfactory results with the traditional fusion techniques, they developed new ones. The continued evolution of lumbosacral fusion has involved the use of hardware or instrumentation in attempting to achieve either stability and thus fusion or correction of deformity and stability followed by fusion. When one considers the numbers of patients who have been treated surgically and followed for decades, it is amazing that it is still not possible to garner a strong scientific consensus on the efficacy of lumbosacral fusion from the literature. Various studies have been conducted over the past several decades and have determined that satisfactory results were obtained in 60% of the cases with disc excision alone and 70% satisfactory results in the fusion group. The conclusion was that despite the slightly better results in the fusion group, the morbidity risk from the fusion procedure meant that the indicated operation was disc excision alone with the recommendation that fusion be performed later if the patient failed with persistent symptoms secondary to instability or degenerative changes. Another study that looked into all aspects of instability whether in the vertical plane (narrowing, olisthesis), the horizontal plane (articular process disease), the frontal plane (scoliosis), and the sagittal plane (spondylolisthesis, compression fracture) concluded that only about one-third of these patients should be fused primarily. However, based upon my experience as an orthopedic surgeon, I have concluded that the ambiguous results from the earlier studies were the result of inadequate, cumbersome, and poorly designed instrumentation for achieving fixation in aid of lumbar fusion.

One can well ask, why use instrumentation in lumbosacral fusion. Fusion is performed in the unstable spinal segment that one wants immobile. Internal fixation increases rigidity and results in a high rate of fusion. This increased fusion rate and decreased pseudarthrosis rate give better results and can significantly reduce postoperative pain and time for convalescence. Spinal instrumentation also allows correction of deformity and maintenance of that correction during consolidation by fusion. Although there are no generally accepted answers to the question of what are the general indications for instrumentation, it is possible to propose a logical schema to guide the spinal surgeon in making these important decisions. The primary considerations are the magnitude of instability, the plane of deformity, and the available intact anatomy.

The past decade or two has seen an extensive development of internal fixation devices for the lumbar and lumbosacral spine. The most common rationale for using such devices is to reduce the incidence of pseudarthrosis after bone grafting. Another rationale (typically for trauma management) is to maintain intervertebral alignment to protect the neural elements until healing occurs. One of the early fixation methods was the placement of screws obliquely across each facet joint involved in the grafting. However, the pseudarthrosis rate was unacceptably high. Numerous other types of devices that variously include plates, wires, rods, bolts, hooks, and, of course screws, have evolved since that time and have resulted in a plethora of devices being available for use by the orthopedic surgeon. Although not provided by all these devices, the ideal device would provide internal alignment and fixation not just in any one of the various planes of movement but in a full, three-dimensional construct.

Numerous patents have been issued for various types of spine fixation devices. These devices employ different mechanical apparatus for enabling the surgeon to selectively adjust the alignment of the patient's spine and then to secure that alignment with the spine fixation device. Edwards (U.S. Pat. No. 4,569,338) discloses a sacral fixation screw having an opening through the head of the screw. A rod-mounted hook is mountable to the opening to interconnect the rod to the sacrum for spinal fixation purposes.

Steffee (U.S. Pat. Nos. 4,648,388 and 4,719,905 discloses a rod, a plurality of clamps, and a plurality of fastener assemblies. The clamps are fastened to selected vertebra and the clamps are tightened against the rod which has been selectively bent to conform to a preselected contour to hold the spine in the desired orientation.

Howland et al (U.S. Pat. No. 4,653,481) disclose a plurality of screw clamp assemblies that are inserted into the vertebral body through the pedicle and are used as anchors for rigid rods which have been selectively bent to conform to a preselected contour to hold the spine in the desired orientation.

Puno et al (U.S. Pat. No. 4,805,602) disclose a transpedicular screw and rod system for the internal fixation of the spine. The rod is held in position against the vertebral lamina by an anchor which is secured to the vertebrae by the transpedicular screw.

Sherman (U.S. Pat. No. 4,887,596) discloses an open backed pedicle screw for use in internal spinal fixation. The open back includes a yoke for receiving a rod and a clamping mechanism for clamping the rod against a cusp in the yoke while permitting angular adjustment between the rod and the yoke.

Gotzen et al (U.S. Pat. No. 4,944,743) disclose an implantable fixation device having a support bar having right-hand threads on one end and left-hand threads on the other end. Jaw supports are threadedly mounted on the respective threaded ends. Bolt jaws are secured to the jaw supports and affixed to intact vertebral bodies of the spinal column.

Gaines, Jr. (U.S. Pat. No. 4,950,269) discloses a spinal column fixation device for connecting vertebrae. The device includes a pedicle screw and a mounting system for mounting a rod to the head of the screw. A cap is engageable on the screw head and is used to retain the rod to the screw.

Krag et al (U.S. Pat. No. 4,987,892) disclose a spinal fixation device wherein at least two pedicle screws are interconnected by a rod. Clamps adjustably secure the rod to the pedicle screws.

Cotrel (U.S. Pat. No. 5,005,562) discloses a spinal fixation device including pedicle screws, and sublaminar hooks interconnected by rods. The pedicle screws and the sublaminar hooks are configured with an open, threaded yoke into which a set screw is threadedly inserted to secure the rod to the pedicle screw and the sublaminar hook.

However, my experience has shown that each of these prior art devices are either cumbersome to implant, difficult to adjust, or require undue surgical time in their implantation. Further, since there is such a wide variation in spinal dimensions and availability of suitable attachment sites, certain of these devices have only limited application. Another problem equally important is that of accurate placement of the pedicle screws followed by subsequent adjustment of the interconnecting rods, wires, hooks, etc., once the pedicle screws are in place.

In view of the foregoing, it would be a significant advancement in the art to provide a spinal fixation apparatus and method that is highly adaptable in its placement, easily adjustable after securement of the pedicle and/or sacral screws, and provides ample support or fixation in all planes. It would also be an advancement in the art to provide a spinal fixation apparatus and method wherein the pedicle screws are quickly and accurately placed for providing the optimal securement of the screws. Such a novel spinal fixation apparatus and method is disclosed and claimed herein.

BRIEF SUMMARY AND OBJECTS OF THE INVENTION

This invention is a novel spinal fixation apparatus and method and includes specially designed pedicle screws, sacral screws, sacral rods, lateral rods, sublaminar hooks, spinous process hooks, and attachment systems. Included is a burr guide for the preparation of the site for placement of the pedicle screw. A sacral screw guide provides for the accurate placement of the sacral screws. The sacral screws and sacral rods are designed to interlock. All parts can be selectively interlocked in an almost infinite number of orientations to provide the spinal fixation apparatus of this invention with an almost infinite variability in placement and subsequent securement, limited only, of course, by the relatively fixed number of attachment points for the novel spinal fixation apparatus of this invention.

It is, therefore, a primary object of this invention to provide improvements in spinal fixation apparatus.

Another object of this invention is to provide improvements in the method for fixation of a spine for fusion.

Another object of this invention is to provide a sacral screw and a lumbosacral rod wherein the sacral screw threadedly interlocks with the lumbosacral rod.

Another object of this invention is to provide an interlock for interlocking a lateral rod to a longitudinal rod in an almost infinite number of positions.

Another object of this invention is to provide a burr guide for quickly and accurately implanting the pedicle screw into the pedicle of the vertebrae.

Another object of this invention is to provide a novel sacral screw guide for accurately directing the sacral screw into the sacrum.

Another object of this invention is to provide a novel sublaminar hook for attachment to the lateral rod and in engagement with the laminar process.

Another object of this invention is to provide a spinous process hook for engagement with the spinous process.

Another object of this invention is to provide a novel pedicle screw for anchoring a rod to the vertebral body either directly into the vertebral body or through the pedicle.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
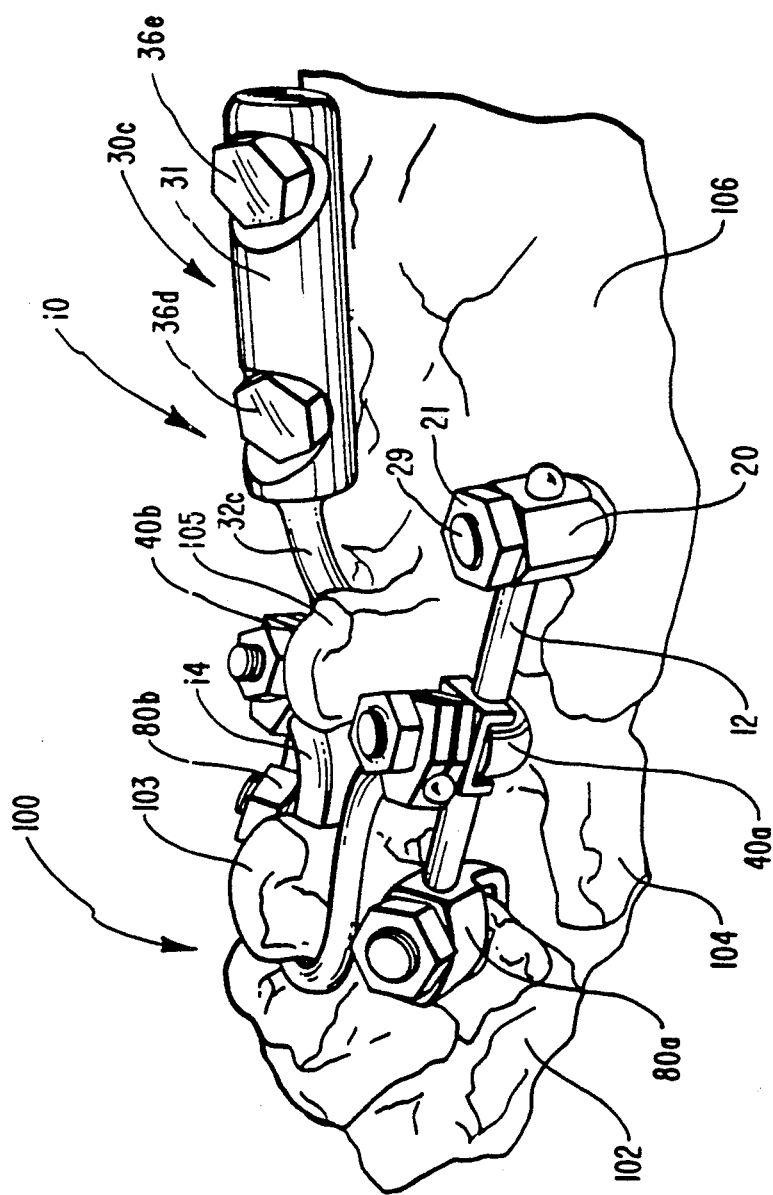
FIG. 1 is a perspective view of the novel spine fixation apparatus of this invention shown in the environment of a portion of the lumbosacral spine.

The invention is best understood by reference to the drawing wherein like parts are designated by like numerals throughout in conjunction with the following description.

General Discussion

The underlying rationale for spinal fusion is to (a) restore the integrity of the spine or to replace missing bone stock, i.e., fracture, tumor, infection; (b) produce an arthrodesis that will suppress undesired movement between two or more bony elements that are the source of pain; maintain correction of spinal deformity or to prevent progression of deformity. In general, this arthrodesis is produced by using a bone graft that will heal and mature, binding the involved elements intimately. Arthrodesis requires in most instances a period of immobilization to achieve this end. Importantly, the key factor in predicting successful fusion is the amount of instability; that is, if instability is moderate and bone stock good, the proportion of easy primary fusion will increase. This goal is readily accomplished using the novel apparatus and method of this invention.

Since fusion is performed in the unstable spinal segment that one wants immobile, the use of the internal fixation apparatus increases rigidity and gives a higher rate of fusion. This resultant increased fusion rate and decreased pseudarthrosis rate give better results and can ease postoperative management regimens. Therefore, spinal instrumentation allows correction of deformity and rigid fixation of that correction during consolidation by fusion.

The novel spinal fixation apparatus and method of this invention enables the surgeon to securely immobilize the desired number of vertebrae thereby providing a stable condition for the ingrowth of bone tissue to achieve true spinal fixation. Importantly, the spinal fixation components are configured to reduce, if not eliminate, the incremental movement or micromotion between the various components. For example, the sacral screw is threadedly engaged to the sacral rod thereby effectively eliminating the micromotion customarily found between these two components. Further, the sacral rods in one embodiment of my invention are securely mounted to the sacrum by the angular orientation of the sacral crews to the sacral rod and to each other. This allows the surgeon to advantageously utilize the greatest mass of bone in the sacrum to achieve optimal fixation of the sacral rod to the sacrum. The pedicle screw is designed to achieve optimal fixation between the pedicle screw and the vertebrae to which it is affixed. A tapered shoulder on the pedicle screw allows it to be countersunk into the pedicle to provide a greater support against transverse forces applied against the pedicle screw. The pedicle screw is also specifically designed to anchor securely through the pedicle into the vertebral body and to securely engage the rod portion of either the sacral rod or a longitudinal rod in a tight, non-release fashion to the vertebra.

I have also devised my novel lumbar spinal fixation apparatus with a high degree of adaptability so that it is a simple matter for the surgeon to adapt the various components of my system to meet the support requirements of almost any spinal condition encountered. My rod and interlink system also allows the surgeon to place supportive rods at almost any location along the length of the spinal column being treated. I have also devised sublaminar hooks that can be securely mounted at any preselected position along the length of a longitudinal rod. This allows the surgeon substantial latitude in placement of the sublaminar hooks to achieve optimal spinal support. The sublaminar hooks work in cooperation with at least one of the novel spinous process hooks to securely fix the specific vertebra in the desired orientation.

Spinal Fixation System

Referring now to FIG. 1, a first, presently preferred embodiment of the novel spine fixation apparatus of this invention is shown generally at 10 and includes a longitudinal rod 12, a lateral rod 14 bent into a spinous process hook, a pedicle screw 20, a sacral rod 30c, a pair of interlinks 40a and 40b, and a pair of sublaminar hooks 80a and 80b. The spine is shown schematically at 100 and includes vertebrae 102 and 104 extending from the sacrum 106. Vertebra 102 has a spinous process 103 while vertebra 104 has a spinous process 105.

As shown herein, spine fixation apparatus 10 is designed to securely fix the orientation of vertebra 102 relative to sacrum 106. This is done by securely mounting pedicle screw 20 and sacral rod 30c to sacrum 106 and then securely engaging vertebra 102 between spinous process hook 14 and sublaminar hooks 80a and 80b. Spinous process hook 14 and sublaminar hooks 80a and 80b are each securely engaged to sacrum 106 through each of pedicle screw 20 (by means of longitudinal rod 12) and sacral rod 30c (by means of rod 32c). Importantly, the placement of engagement of spinous process hook 14 and sublaminar hooks 80a and 80b is selectively adjustable to allow the surgeon to adjustably position vertebra 102 relative to sacrum 106.

In this particular embodiment, pedicle screw 20 is shown in combination with sacral rod 30c as the devices for providing attachment of their relative components to sacrum 106. Clearly, a second sacral rod 30a (FIGS. 2-4) or, sacral rod 30b (FIG. 3) could be mounted to sacrum 106 in place of pedicle screw 20 to achieve the desired degree of fixation. However, pedicle screw 20 is shown herein to further illustrate the adaptability of pedicle screw 20 to varying fixation situations, as will be discussed further hereinafter.

Sacral rod 30c includes a rod 32c extending coaxially from a body 31 and provides the site for fixation of interlink 40b and sublaminar hook 80b to sacral rod 30c. Rod 32c may be selectively bent by the surgeon (not shown) to achieve the desired orientation of rod 32c (hence, interlink 40b and sublaminar hook 80b) relative to spine 100. Sacral rod 30c is affixed to sacrum 106 by a pair of bone screws 36d and 36e which pass through body 31c and into threaded engagement with sacrum 106. Bone screws 36d and 36e also threadedly engage body 31c as will be described more fully hereinafter.

Sacral Rods and Bone Screws

Referring now to FIGS. 2A-2D, another embodiment of a novel sacral rod of this invention is shown generally at 30a and includes a body 31a having an enlarged diameter and a rod 32a having a reduced diameter extending coaxially from the end thereof. Body 31a includes a pair of threaded ports 34a and 34b therethrough, the function of which will be discussed more fully hereinafter. Countersinks 35a and 35b are formed at each of threaded ports 34a and 34b, respectively. The axis of each of threaded ports 34a and 34b as well as that of countersinks 35a and 35b is angularly offset from the axis of sacral body 31 as shown by the angle 33a and 33b in FIG. 2C.

Bone screws 36a and 36b each include threaded shafts 37a and 37b which extend from threaded necks 38a and 38b, respectively. Bone screws 36a and 36b are designed to pass downwardly through threaded ports 34a and 34b with threaded necks 38a and 38b being threadedly engaged in threaded ports 35a and 35b with heads 39a and 39b seated firmly in countersinks 35a and 35b, respectively.

Figure 2A:
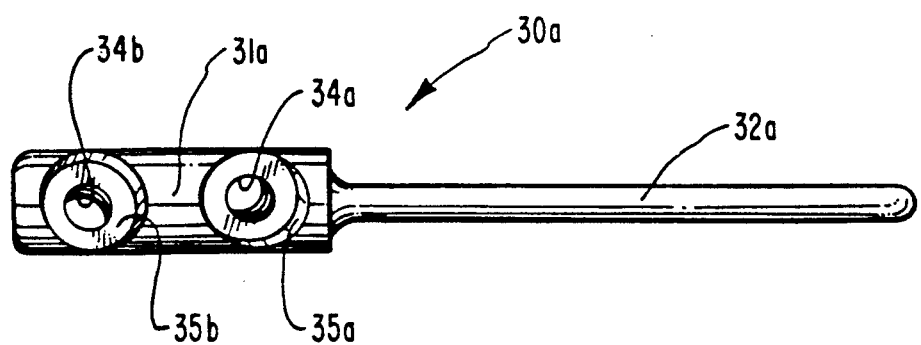
FIG. 2A is a plan view of one embodiment of a sacral rod.
Figure 2B:
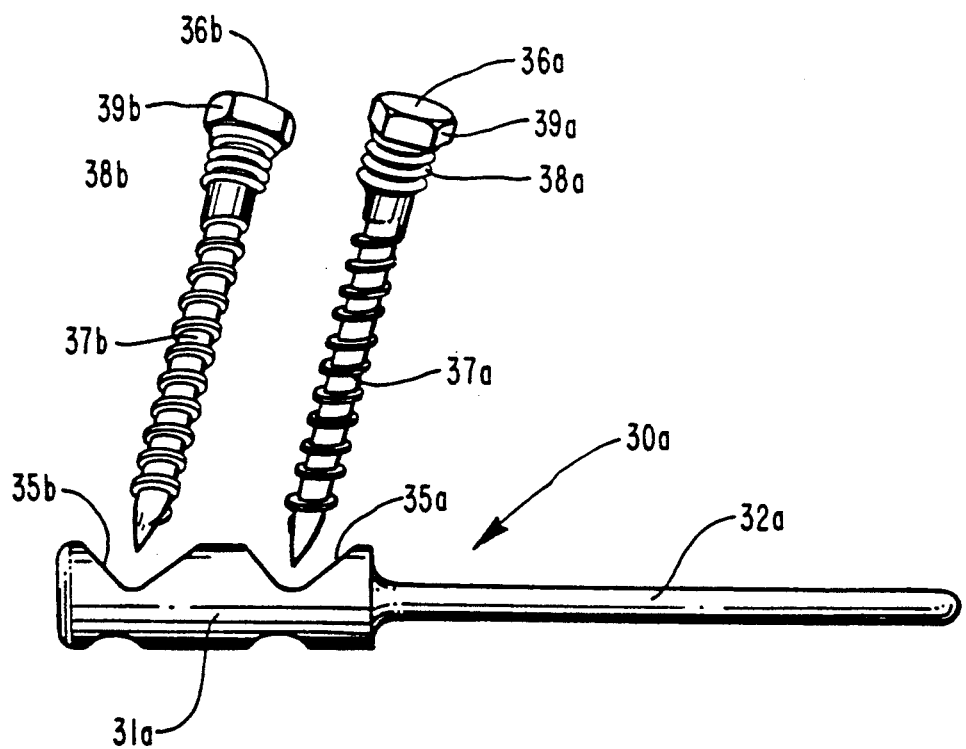
FIG. 2B is a side elevation of the sacral rod of FIG. 2A shown with one embodiment of a pair of bone screws.
Figure 2C:
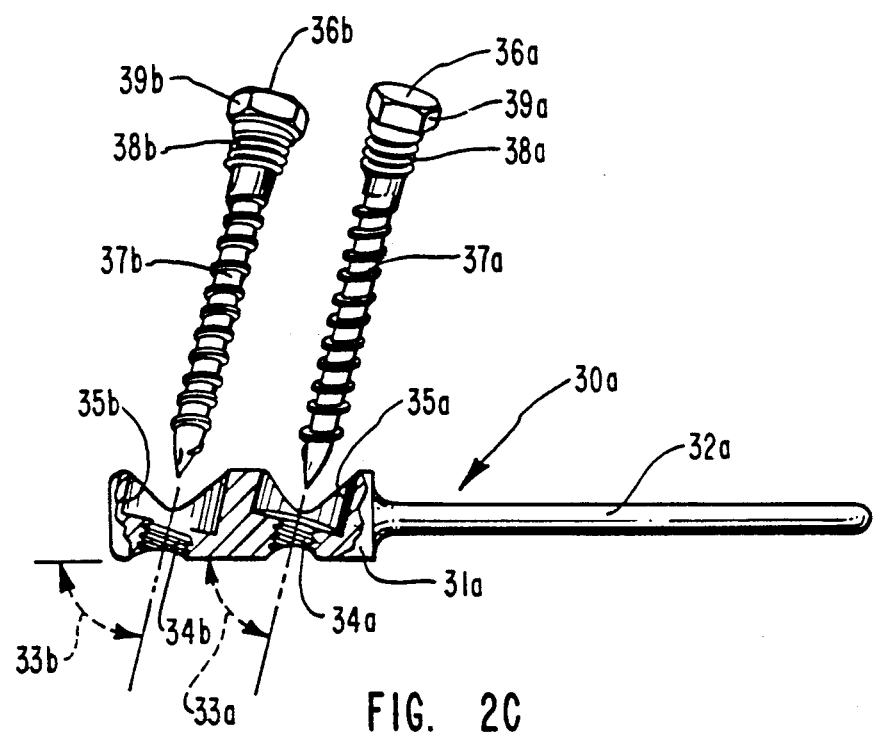
FIG. 2C is a partial cross sectional view of the sacral rod of FIG. 2B showing the angular relationship between the axis of the bone screws and the axis of the sacral rod.
Figure 2D:
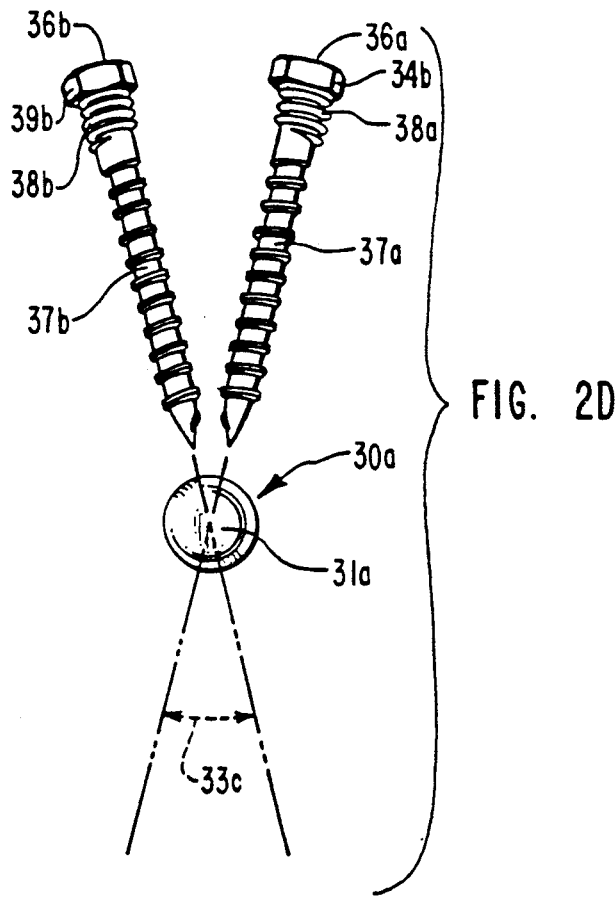
FIG. 2D is an end view of the sacral rod and bone screws of FIG. 2B showing the angular offset between the two bone screws.
Figure 3:
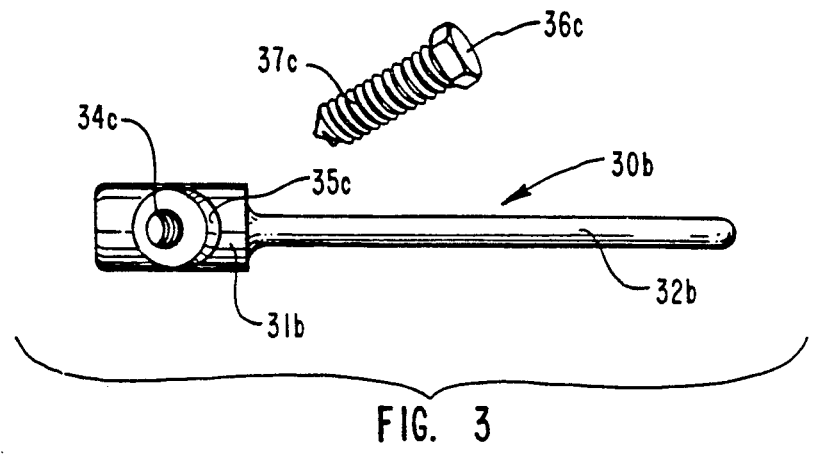
FIG. 3 is a plan view of a second embodiment of the sacral rod of my invention shown in the environment of another embodiment of a bone screw.

Referring now to FIG. 3, another embodiment of the sacral rod is shown as sacral rod 30b and is configured with a shorter sacral body 31b having a rod 32b extending coaxially therefrom. Sacral body 31b has a single countersink 35c therein with a threaded port 34c in the bottom thereof. The tread pitch and the diameter of port 34c is the same for that of threaded ports 34a and 34b (FIGS. 2A and 2C).

Shown in combination with sacral rod 30b is a bone screw 36c which is configured with a threaded body 37c, the diameter and thread pitch of which matingly cooperates with the threads of threaded throughbore 34c. Bone screw 36c is designed to securely interlock sacral rod 30c to sacrum 106 in a snug, tight fit relationship to essentially eliminate all micromotion between sacral rod 30c and sacrum 106. The thread pitch of the threads on threaded body 37c closely approximates a standard machine thread and has a more shallow pitch (more threads per unit length) than a standard bone screw such as shown by threaded body 37a and 37b of bone screws 36a and 36b, respectively, of FIGS. 2B-2D.

The thread pitch of bone screw 36a and 36b is a standard bone screw pitch and is specifically designed for its greater resistance to pull forces exerted longitudinally along the axis. This is referred to in the art as the pull out strength of the particular bone screw. Clearly, therefore, the thread pitch of bone screw 36c has a weaker pull out strength because the more shallow thread pitch provides less "bite" into the cancellous bone. However, I have found that pull out strength is less important for the application of the novel spinal fixation apparatus and method of my invention since I require greater strength in relation to transverse forces imposed on bone screw 36c versus the customary longitudinal forces encountered in a standard pull out test. Further, the diameter of bone screw 36c is greater than that of bone screws 36a and 36b and with this greater diameter bone screw 36c presents a greater surface area against which the cancellous bone (not shown) will be engaged thereby providing substantially increased resistance to movement or micromotion under transverse forces.

However, note also that bone screw 36c can be used interchangeably with bone screws 36a and 36b as required by the surgeon. This is possible by reason of the fact that threaded ports 34a, 34b, and 34c are identical in size and thread pitch.

Figure 4:
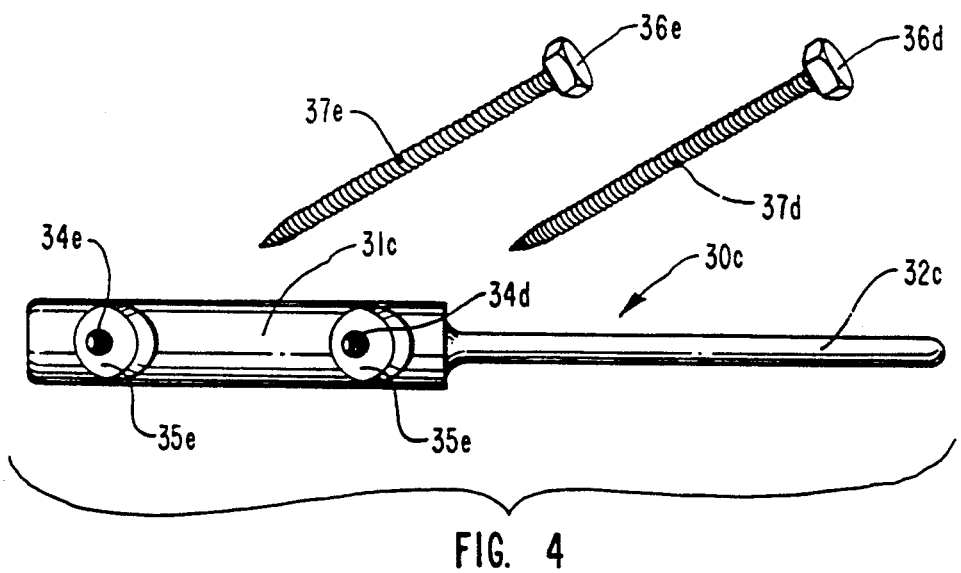
FIG. 4 is a plan view of a third embodiment of the sacral rod of my invention shown in the environment of a third embodiment of the bone screws of my invention.

Referring now to FIG. 4, the third embodiment of the sacral rod is shown as sacral rod 30c (see also, FIG. 1) which is configured with an elongated sacral body 31c and having a rod 32c extending coaxially from sacral body 31c. Sacral body 31c includes countersinks 35d and 35e with threaded throughbores 34d and 34e in the bottom thereof. Note that countersinks 35d and 35e are of the same diameter and depth as countersinks 35a and 35b (FIGS. 2A-2C) and countersink 35c (FIG. 3) whereas threaded throughbores 34d and 34e each have a smaller diameter. This smaller diameter is designed to accommodate smaller diameter bone screws 36d and 36e having a threaded body 37d and 37e the threads of which matingly cooperate with threaded throughbores 34d and 34e respectively.

The particular relationship of sacral rod 30c and bone screws 36d and 36e is specifically designed to allow the surgeon (not shown) greater flexibility in affixing sacral rod 36c to sacrum 106 in order to more readily adapt the novel spinal fixation apparatus and method of this invention to the particular circumstances encountered by the surgeon during the surgical procedure.

Referring now to all of FIGS. 2A-2D, FIG. 3, and FIG. 4, the various features of each of sacral rods 30a-30c can be selectively interchanged to accommodate the various types of bone screws 36a-36e in order to provide the surgeon with the greatest possible degree of flexibility in implanting my unique spinal fixation apparatus. For example, bone screw 36c can be used with either of sacral rods 30a or 30b while either of sacral rods 30a or 30b can be modified to accommodate the use of bone screws 36d and 36e therewith. Clearly, of course, the primary criteria for selection of the specific sacral rod or bone screw combination will depend upon the particular conditions encountered during the surgical procedure.

Pedicle Screw

Figure 6A:
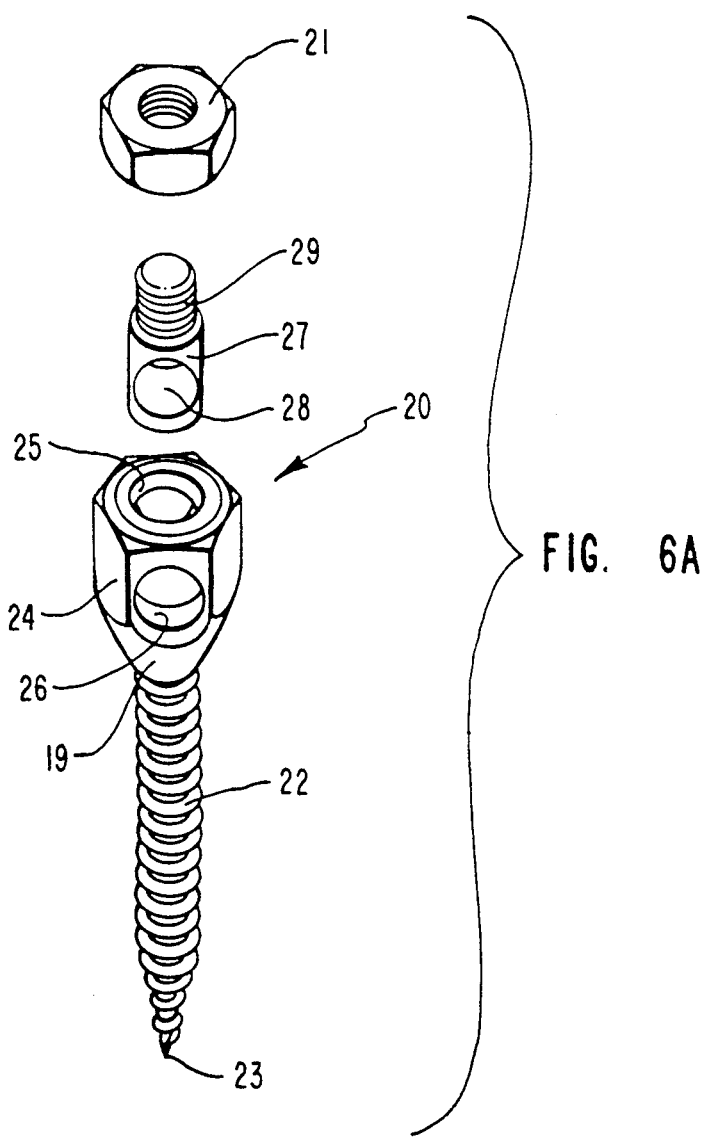
FIG. 6A is an exploded perspective view of the pedicle screw.
Figure 6B:
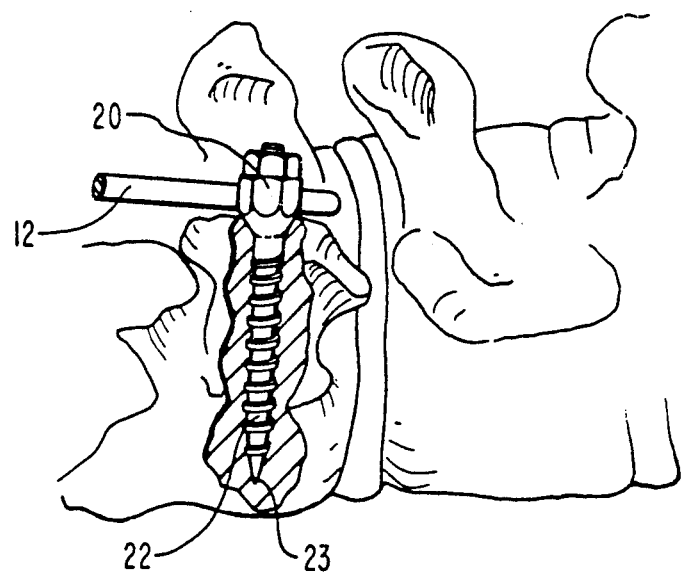
FIG. 6B is a side elevation of a pedicle screw embedded through the pedicle of a vertebral body with portions broken away to reveal internal features.
Figure 6C:
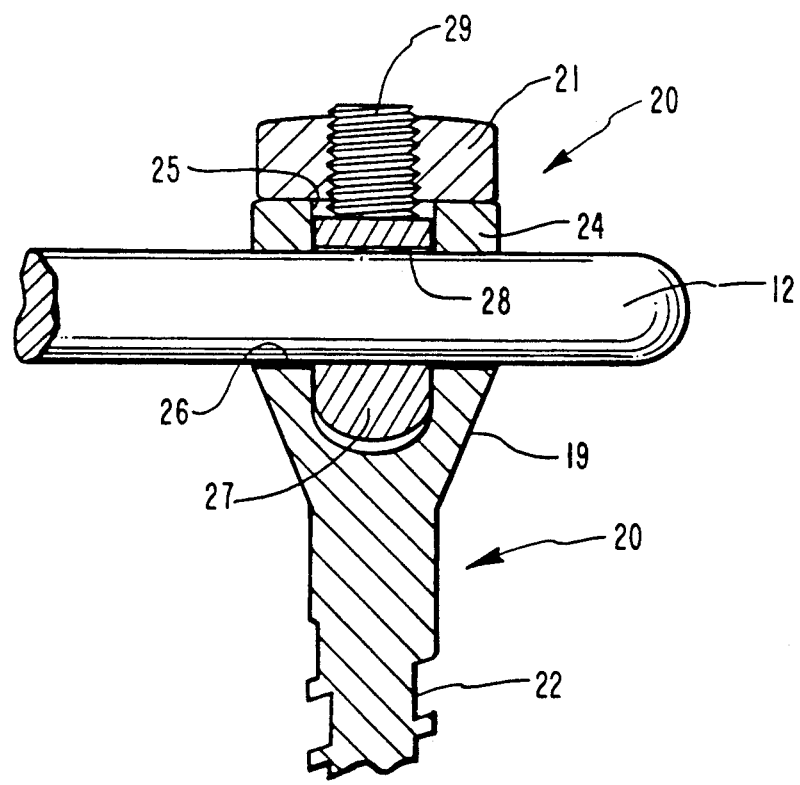
FIG. 6C is an enlarged, fragmentary, cross sectional view of the clamping mechanism of the pedicle screw for securing a rod to the pedicle screw.

Referring now to FIGS. 6A-6C, the novel pedicle screw of this invention is shown generally at 20 and includes a screw body 22, a pointed tip 23, an anchor head 24, and a tapered shoulder 23 between anchor head 24 and screw body 22. Screw body 22 is a conventional bone screw having threads that are known to securely anchor pedicle screw 20 in bone. Anchor head 24 is configured as an elongated, hexagonal head having a coaxial, blind bore 25 and a transverse, throughbore 26. An anchor body 27 is telescopically received in blind bore 25 by having an external diameter that is slidingly received in a snug fit relationship in the internal diameter of blind bore 25. Anchor body 27 includes a throughbore 28 that is configured to reside in alignment with throughbore 26 when anchor body 27 is inserted into blind bore 25 of anchor head 24. A coaxial, threaded boss 29 extends from the end of anchor body 27 and is designed to receive a threaded hex nut 21 thereon in threaded relationship.

Pedicle screw 20 is designed to be inserted downwardly through the pedicle into the vertebral body to thereby provide a solid fixation for the particular rod engaged therewith. This feature is best seen in FIG. 6B.

Figure 6D:
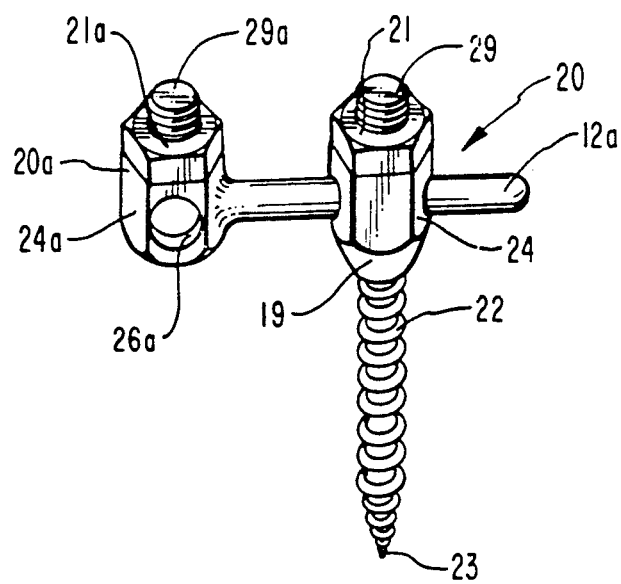
FIG. 6D is a perspective view of a pedicle screw with a rod clamp engaged therein.

Referring now to FIG. 6D, a rod clamp 20a is shown mounted on the end of a length of an anchor arm 12a which, in turn, is engaged by pedicle screw 20. Rod clamp 20a includes a second anchor head 24a which is essentially identical to anchor head 24 in that it includes a throughbore 26a and an anchor body (not shown) similar to anchor body 27 (FIGS. 6A-6C). Threaded boss 29a is threadedly engaged by a nut 21a. Rod clamp 20a is rotatable about the axis of anchor arm 12a while pedicle screw 20 is rotatable about the axis of screw body 22 thereby allowing the surgeon (not shown) to orient a rod (not shown) engaged in throughbore 26a of rod clamp 20a in an almost infinite number of degrees of orientation.

Universal Interlink

Figure 7:
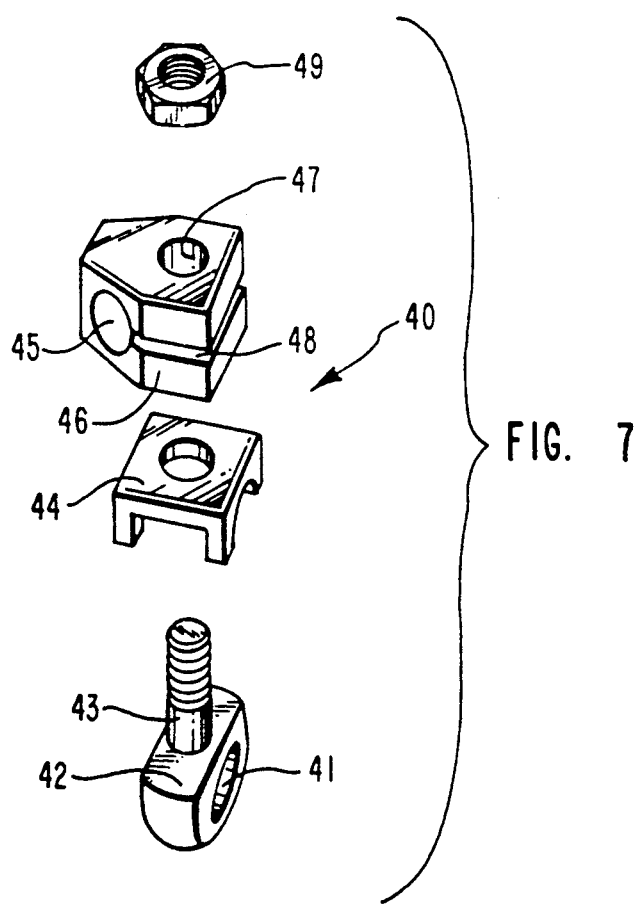
FIG. 7 is an exploded, perspective view of another embodiment of an interlink clamp.

Referring now to FIG. 7, a first preferred embodiment of the novel, universal interlink of this invention is shown generally at 40 and includes a bolt vise 42, a cleat 44, a rod clamp 46, and a nut 49. Bolt vise 42 is configured with a throughbore 41, the diameter of which is designed to slidingly receive therethrough any one of rod 12, 14, or 32c (FIG. 1) or anchor arm 12a (FIG. 6D) of the novel spinal fusion apparatus 10 of this invention. Bolt vise 42 cooperates with cleat 44 to securely clamp the rod engaged in throughbore 41 when bolt 43 is tightened by nut 49. Cleat 44 is configured with an inverted, U-shaped profile extending downwardly from each side of the central body. The clamping action of bolt vise 42 is achieved by the particular rod in throughbore 41 being securely engaged between bolt vise 42 and cleat 44.

Rod clamp 46 is configured as two joined plates formed around a transverse throughbore 45 and separated by a slot 48. Rod clamp 46 is sufficiently resilient across slot 48 to create a clamping action on a rod passing through throughbore 45. A hole 47 is formed through clamp 46 and is designed to receive bolt 43 therethrough. The lower surface of clamp 46 is designed to rest against cleat 44 when bolt 43 is passed upwardly through cleat 44 and hole 47 in rod clamp 46. Tightening nut 49 on bolt 43 closes slot 48 of clamp rod 46 constricting the internal diameter of transverse throughbore 45 while at the same time pulling bolt vise 42 into the confines of cleat 44 so that the extended profile of throughbore 41 is constricted by cleat 44. In this manner, two rods inserted through each of throughbore 45 and throughbore 41 are securely clamped by universal interlink 40. Importantly, the angular orientation of the axis of throughbore 41 can be selectively positioned at any one of an infinite angular orientations in the plane of rotation of the axis of bolt 43. Further, the plane of rotation of the axis of throughbore 45 about the axis of bolt 43 forms a plane that is parallel to the plane of rotation of the axis of throughbore 41 and separated only by the distance along bolt 43. However, the axis of throughbore 41 is offset from the axis of throughbore 45 to accommodate the use of a single bolt 43 to provide the foregoing clamping action of universal interlink 40.

Figure 8:
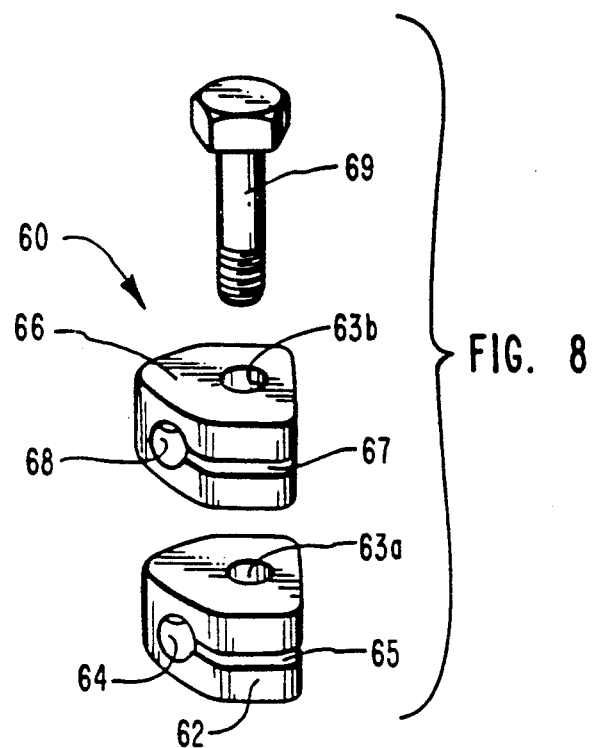
FIG. 8 is an exploded, perspective view of a second embodiment of an interlink clamp.
Figure 9A:
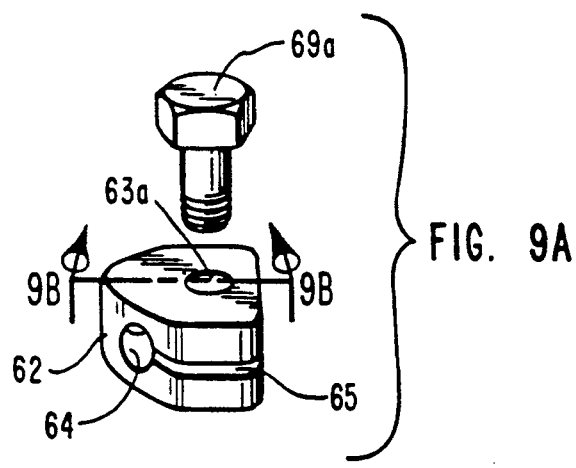
FIG. 9A is an exploded, perspective view of another embodiment of an interlink clamp shown in the environment of a bolt.
Figure 9B:
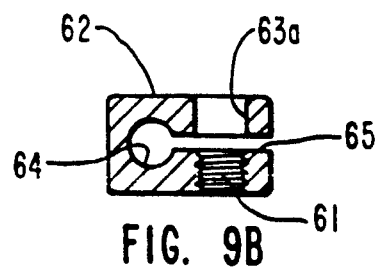
FIG. 9B is a cross sectional view of the interlink clamp of FIG. 9A taken along lines 9B—9B of FIG. 9A.
Figure 16:
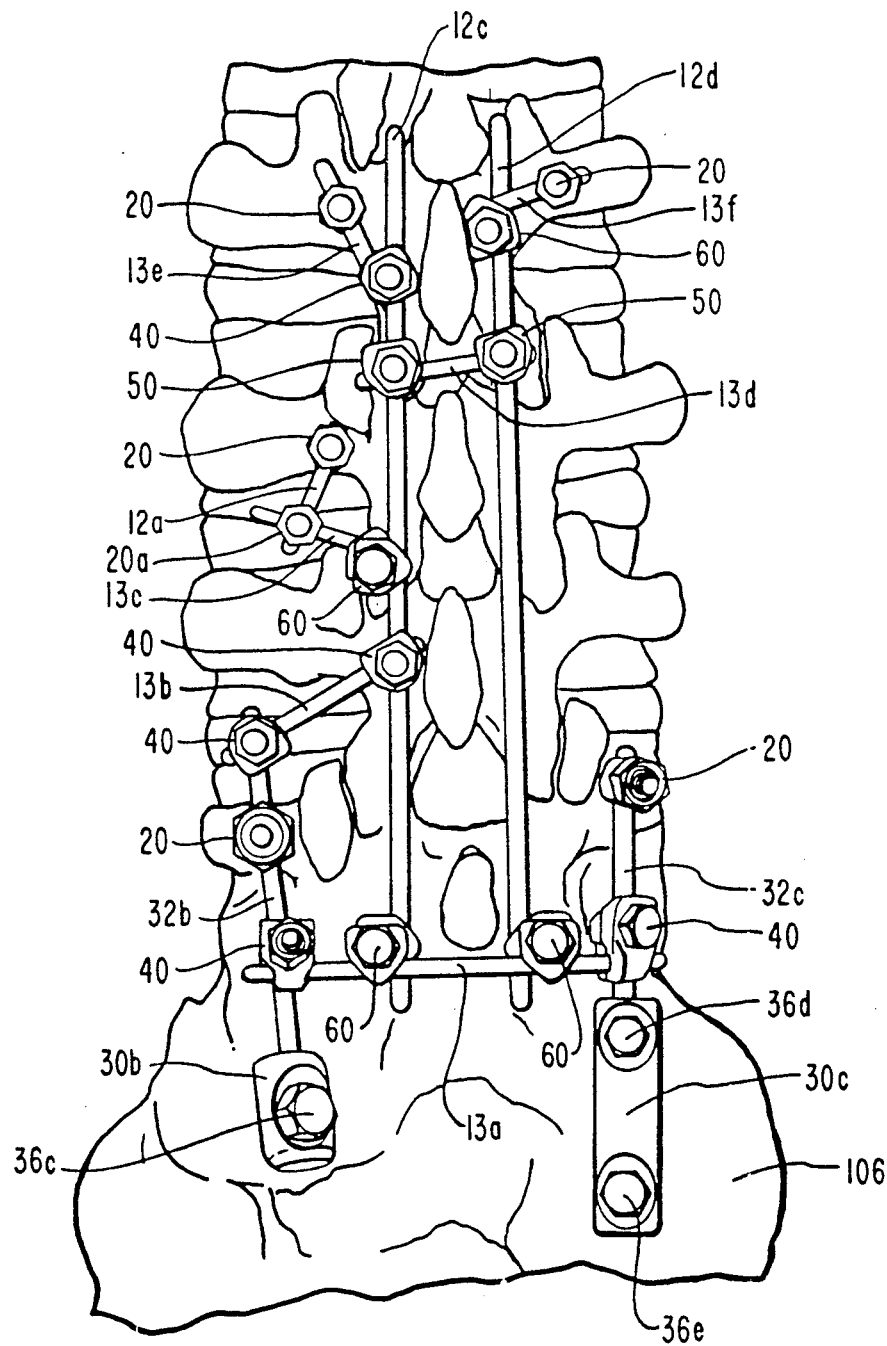
FIG. 16 is a plan view of the novel spinal fixation apparatus of my invention shown in the environment of the sacrum and a portion of the sacral spine.

Referring now to FIGS. 8, 9A and 9B, a second preferred embodiment of the novel, universal interlink of this invention is shown generally at 60 and includes a lower clamp 62, an upper clamp 66 and a bolt 69. Lower clamp 62 includes a bolt hole 63a and a transverse throughbore 64 having an open slot 65 along its length. Similarly, upper clamp 66 includes a bolt hole 63b and a transverse throughbore 68 having an open slot 67 along its length. Threads 61 in the bottom of bolt hole 63a (see FIG. 9B) receive corresponding threads on bolt 69 to allow upper clamp 66 to be pressed against lower clamp 62 creating a clamping action against rods (not shown) engaged in each of transverse throughbores 68 and 64, respectively. Universal interlink 60 accommodates the interlinking of various rods and spinous process hooks in an almost infinite range of orientations. Advantageously, the various versions of the novel universal interlink of this invention, universal interlink 40 and universal interlink 60, provide the surgeon (not shown) with a highly adaptable, readily usable and adjustable device for interlinking various components of the novel spinal fixation apparatus 10 of this invention (FIGS. 1 and 16).

Figure 5A:
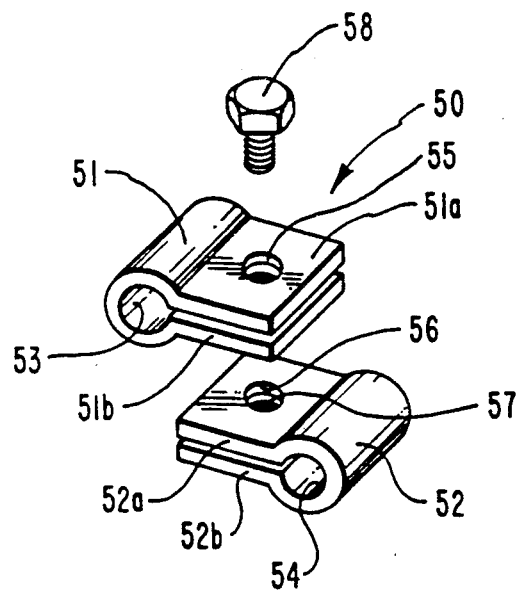
FIG. 5A is an exploded perspective of a first embodiment of the interlink of my invention.

Referring now to FIG. 5A, a third preferred embodiment of the novel interlink of this invention is shown generally at 50 and includes an upper rod clamp 51, a lower rod clamp 52, and a bolt 58 for securing upper rod clamp 51 to lower rod clamp 52 while simultaneously causing upper rod clamp 51 to tightly engage a first rod (not shown) engaged thereby and lower rod clamp 52 to tightly a second rod (not shown) engaged thereby. Upper rod clamp 51 is configured with flanges 51a and 51b extending outwardly from a cylindrical section 53. A hole 55 in flanges 51a and 51b accommodates the passage of bolt 58 therethrough. Lower rod clamp 52 is essentially identical to upper rod clamp 51 by having flanges 52a and 52b extending outwardly from a cylindrical section 54. The only difference is that hole 56 in flange 52b is threaded with threads 57 to accommodate being threadedly engaged by corresponding threads on bolt 58. This is accomplished by placing hole 55 in alignment with hole 56 and passing bolt 58 downwardly into threaded engagement with threads 57. Continued tightening of bolt 58 into threads 57 causes flanges 51a and 51b as well as flanges 52a and 52b to compress together thereby reducing the respective internal diameters of each of cylindrical sections 53 and 54. The angular orientation of the axis of cylindrical section 53 relative to the axis of cylindrical section 54 can be almost infinite, limited only by the interference encountered between cylindrical section 53 and cylindrical section 54. Note that the two rods (not shown) engaged thereby reside in parallel planes separated only by the thicknesses of flanges 51b and 52a.

Rod Clamp

Figure 5B:
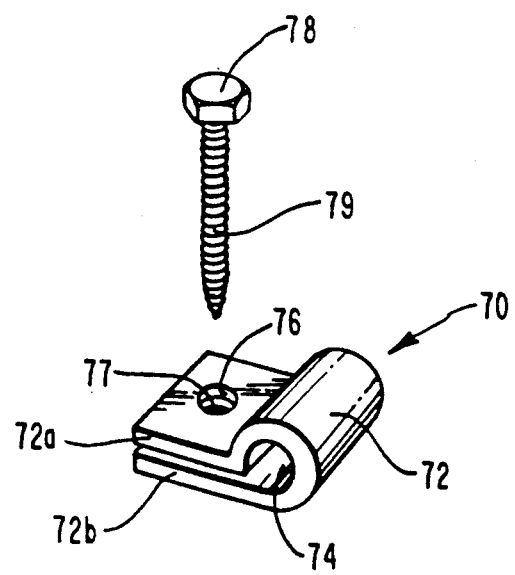
FIG. 5B is an exploded perspective of a rod clamp shown in the environment of a bone screw.

Referring now to FIG. 5B, a rod clamp portion of my spinal fixation system is shown at 70 and includes a single rod clamp 72 having flanges 72a and 72b extending outwardly from a cylindrical section 74. A hole 76 is formed in flanges 72a and 72b with threads 77 formed in flange 72b. Rod clamp 72 differs from rod clamp 52 (FIG. 5A) in that flange 72b extends tangentially outward from cylindrical section 74 versus the mid section thereof with regard to rod clamp 52 (FIG. 5A). This configuration allows rod clamp 70 to be placed in abutment with a vertebral body 83 (FIG. 12) or as a substitute for rod clamp 52 in universal interlink 50 (FIG. 5A).

Figure 12:
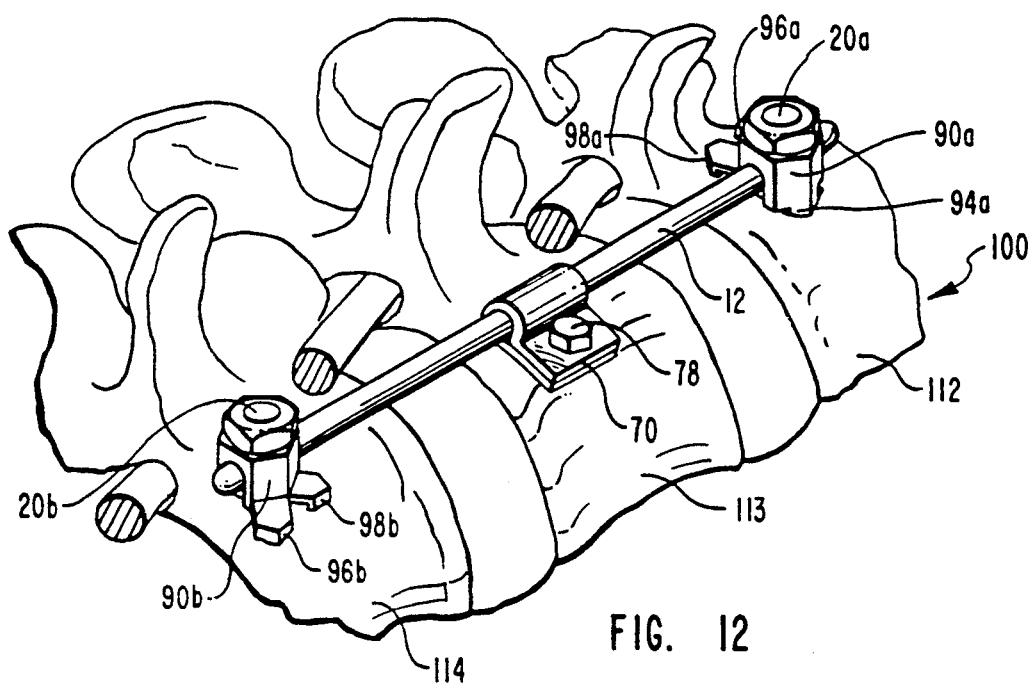
FIG. 12 is a perspective view of the anterior fixation of the spine using two pedicle screws and a rod in combination with a rod clamp and bone screw.

A bone screw 78 is shown and is used to securely engage rod clamp 70 to vertebral body 83 (FIG. 12). Bone screw 78 has threads 79 along the length thereof to threadedly engage threads 77 while at the same time threadedly engaging the cancellous bone of vertebral body 83 (FIG. 12) thereby securely engaging rod clamp 70 to vertebral body 83 while simultaneously clamping rod 12.

Sublaminar Hook

Figure 10:
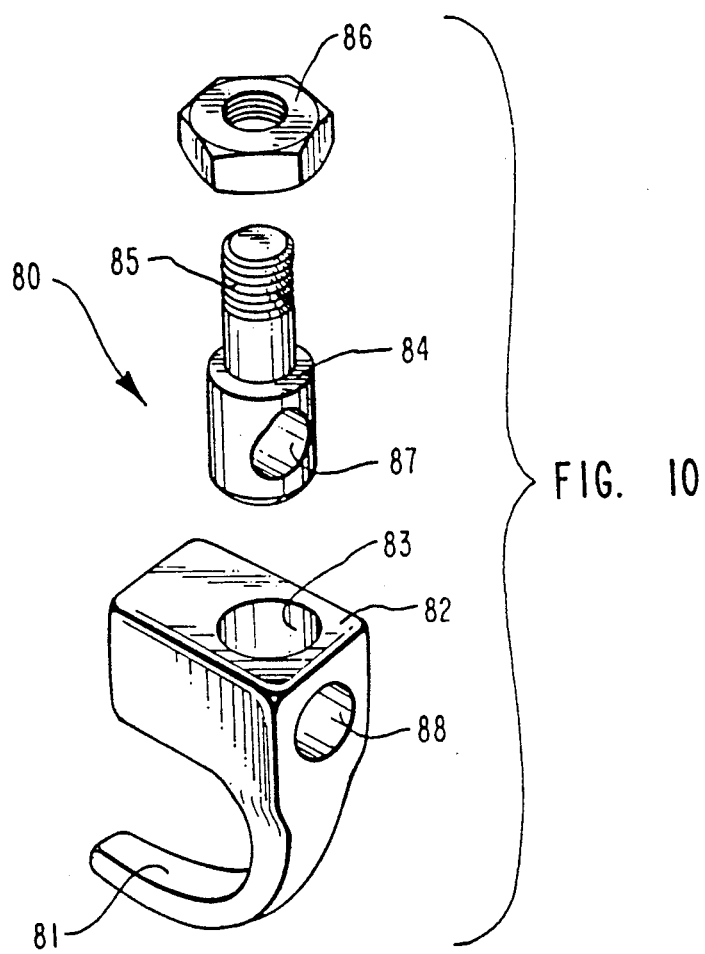
FIG. 10 is an exploded, perspective view of a sublaminar hook.

Referring now to FIG. 10, the novel sublaminar hook of this invention is shown generally at 80 and includes a hook body 82, an anchor body 84 and a nut 86. Hook body 82 includes a hook 81, a throughbore 88 and a blind bore 83. Throughbore 88 is configured to receive rod 12 (FIG. 1) therethrough. Anchor body 84 is configured similarly to anchor body 27 (FIGS. 6A-6D) and has a threaded boss 85 extending coaxially therefrom and a throughbore 87. Anchor body 84 is configured to be inserted into blind bore 83 with throughbore 87 in alignment with throughbore 88. In this manner, a rod 12 (FIG. 1) can be inserted into sublaminar hook 80 and clamped thereto upon tightening nut 86 on threaded boss 85.

Spinous Process Hook

Figure 11:
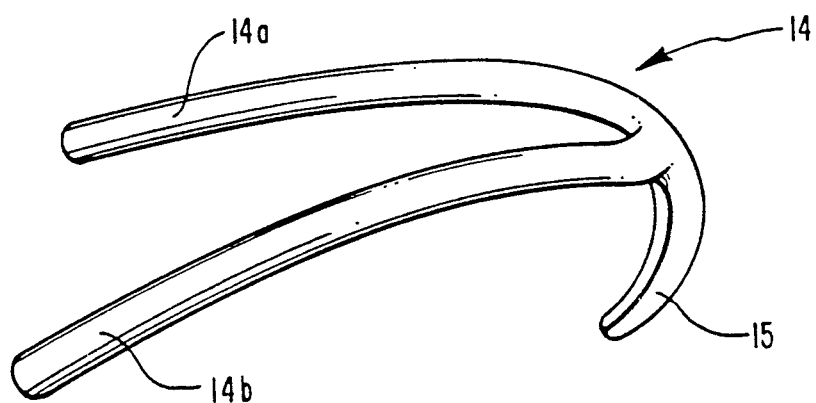
FIG. 11 is a perspective view of a spinous process hook.

Referring now to FIG. 11, spinous process hook 14 is illustrated more clearly to show the various features thereof including the two spaced arms, arms 14a and 14b, along with hook 15 depending downwardly from the U-like juncture between arms 14a and 14b. Arms 14a and 14b are configured with the same cross sectional area as rod 12 (FIG. 1) so as to accommodate arms 14a and 14b being secured by pedicle screw 20 or universal interlink 40 (FIG. 1) thereby providing a broad range of attachment devices for securing the relative position of spinous process hook 14 to spinous process 103 (FIG. 1).

Spinous process hook 14 is configured to engage spinous process 103 (FIG. 1) by spinous process 103 being straddled by arms 14a and 14b with hook 15 contacting the basal portion of spinous process 103. The surgeon (not shown) is then able to place tension forces against spinous process 103 and secure spinous process 103 by clamping arms 14a and 14b with universal interlink 40 or, possibly, even with pedicle screw 20 (FIG. 1). Arms 14a and 14b can also be bent into a preselected configuration as shown in FIG. 1 to achieve the desired degree of fixation for spine 100.

Spinous process hook 14 acts as a tension-like member to place tension against the specific spinous process 103 (FIG. 1) while sublaminar hooks 80a and 80b (FIG. 10), in effect, act as an anchor against the sublamina of vertebra 103 thereby allowing the surgeon (not shown) to securely anchor the specific vertebra in the desired orientation. This combination of tension and anchor serves to engage the specific vertebra in a secure fixation. Adjustability is provided by the ability to adjustably locate universal interlinks 40 and sublaminar hook 14 at any preselected location on either longitudinal rod 12 or sacral rod 32c. Since longitudinal rod 12 and sacral rod 32c are both firmly fixed to sacrum 106, ultimately, vertebra 102 is also firmly anchored relative thereto.

Spinal Fixation

Referring now to FIG. 16, a generalized embodiment of the novel spine fixation apparatus of my invention is shown as a plurality of elements adjustably interconnected to create one possible spine fixation apparatus. In particular, sacral rod 30b is affixed to the left side of sacrum 106 using a bone screw 36c. Correspondingly, sacral rod 30c is affixed to the right side of sacrum 106 using bone screws 36d and 36e. Longitudinal rods 32b and 32c extend coaxially from each of sacral rods 30b and 30c, respectively, and are anchored to the adjacent vertebra by pedicle screws 20. A lateral rod 13a is securely mounted between longitudinal rods 32b and 32c by a pair of universal interlinks 40. Lateral rod 13a provides an anchor point for a pair of longitudinal rods 12c and 12d on the left side and right side, respectively, of the spinal column. A pair of universal interlinks 60 are used to securely engage longitudinal rods 12c and 12d to lateral rod 12a.

Longitudinal rods 12c and 12d provide the structural support framework for this particular embodiment of my spinal fixation apparatus. Although numerous elements are shown as constituting this one embodiment of my spinal fixation apparatus, they can also be combined in numerous variations to create the desired degree and type of fixation for the sacral spine. Accordingly, it is to be clearly understood that the illustrated embodiment of FIG. 16 is strictly for illustrative purposes only and is not necessarily intended as a particular spinal fixation apparatus designed to treat a specific spinal condition. The construct of FIG. 16 is strictly intended to illustrate the unique capability of the various components of my invention for creating an almost unlimited number of variants to the construct of my spinal fixation apparatus. For example, it is extremely difficult for a surgeon to accurately align a plurality of pedicle screws 20 so that a single longitudinal rod 12c or 12d could be mounted directly to each pedicle screw 20. Accordingly, I have provided numerous interlink systems for providing fixation between longitudinal rods 12c and 12d and the respective pedicle screws 20 but also to each other. For example, a universal interlink 40 on the end of longitudinal rod 32b is used to interconnect lateral rod 13b to a second universal interlink 40 on longitudinal rod 12c and thereby provide additional supportive structure to longitudinal rod 12c.

Correspondingly, lateral rod 13c is used to interconnect a universal interlink 60 on longitudinal rod 12c to pedicle screw 20 through a rod clamp 20a engage to lateral rod 13c and, in turn, coupled to pedicle screw 20. This system enables the surgeon (not shown) to interconnect pedicle screw 20 to longitudinal rod 12c without having to align pedicle screw 20 into exact alignment with longitudinal rod 12c.

Alternatively, lateral rod 13e can be used to directly couple longitudinal rod 12c to pedicle screw 20 through the use of universal interlink 40. This arrangement is possible when the angular orientation of pedicle screw 20 is such so as to accommodate lateral rod 13e being directly coupled between pedicle screw 20 and universal interlink 40. A similar situation is also found with respect to lateral rod 13f as it is used to link longitudinal rod 12d directly to pedicle screw 20 through universal interlink 60.

Longitudinal rods 12c and 12d can be selectively coupled together through the use of one or more lateral rods such as is illustrated by lateral rod 13d. Lateral rod 13d is securely engaged by a pair of universal interlinks 50, one on each of longitudinal rods 12c and 12d. Advantageously, lateral rod 13d can be selectively positioned at any suitable location along the length of longitudinal rods 12c and 12d. This feature readily accommodates the secure support of the spine and also provides the surgeon (not shown) with enormous flexibility in providing the necessary construct for the spine.

Anterior Fixation

Referring now to FIG. 12, pedicle screw 20 is shown in combination with a longitudinal rod 12 as an anterior fixation system. In particular, longitudinal rod 12 is anchored at each end to spine 110 by pedicle screw 20a which is mounted to vertebral body 112 and pedicle screw 20b which is mounted to vertebral body 114. Longitudinal rod 12 spans vertebra 113 which is the vertebra of spine 110 requiring fixation relative to vertebra 112 and vertebra 114. Rod clamp 70 is used in combination with bone screw 70 to securely clamp longitudinal rod 12 to vertebra 113.

Pedicle Screw Anchor Cap

Figure 13:
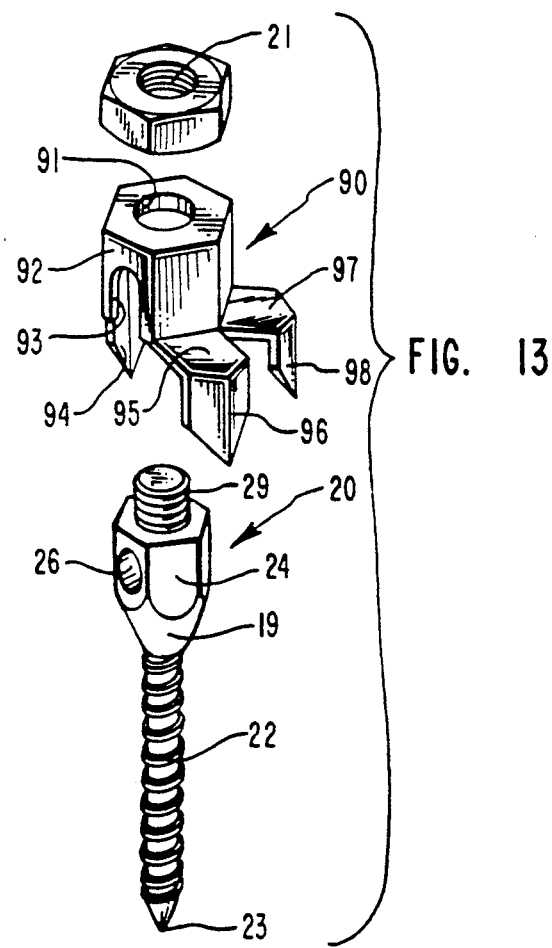
FIG. 13 is an exploded, perspective view of an anchor cap for a pedicle screw in combination with a pedicle screw.

Referring to FIGS. 12 and 13, anchor caps 90a and 90b are used to further reduce any possible micromotion between pedicle screw 20a and vertebral body 112 and pedicle screw 20b and vertebral body 114, respectively. Referring specifically to FIG. 13, anchor cap 90 is configured with a housing 92 adapted to snugly engage anchor head 24 in a close-fitting relationship by telescopically receiving anchor head 24 as anchor cap 90 is pressed downwardly over anchor head 24. A hole 91 in the upper portion of housing 92 allows threaded boss 29 to pass upwardly through hole 91 and thereby present itself to be threadedly engaged by nut 21. Nut 21 securely clamps housing 92 to pedicle screw 20 while simultaneously securely engaging longitudinal rod 12, as described previously.

Anchor cap 90 includes a plurality of downwardly pointed prongs, prongs 94, 96, and 98, which are designed to embed securely into the particular vertebral body, vertebral bodies 112 and 114, to which the particular anchor cap 90 is secured. Prong 94 is formed as a downward extension of housing 92 while prongs 96 and 98 extend downwardly from the respective horizontal flanges 95 and 97. Horizontal flanges 95 and 97 provide improved lateral stability to anchor cap 90 by extending outwardly therefrom and thereby support prongs 96 and 98 in rigid, spaced relationship to anchor cap 90. A slot 93 in opposing sides of anchor cap 90 allows longitudinal rod 12 (FIG. 12) to be engaged in pedicle screw 20 before anchor cap 90 is mounted to pedicle screw 20.

Referring again to FIG. 12, pedicle screw 20a has an anchor cap 90a mounted thereon with prongs 94a, 96a, and 98a embedded in the bone of vertebral body 112. Similarly, pedicle screw 20b has anchor cap 90b mounted thereon with prongs 96b and 98b embedded in the bone of vertebral body 114. The embedment of prongs 94, 96, and 98 into the bone of the respective vertebral body helps anchor cap 90 to reduce any micromotion between pedicle screw 20 and the respective vertebral body.

Burr Guide

Figure 14:
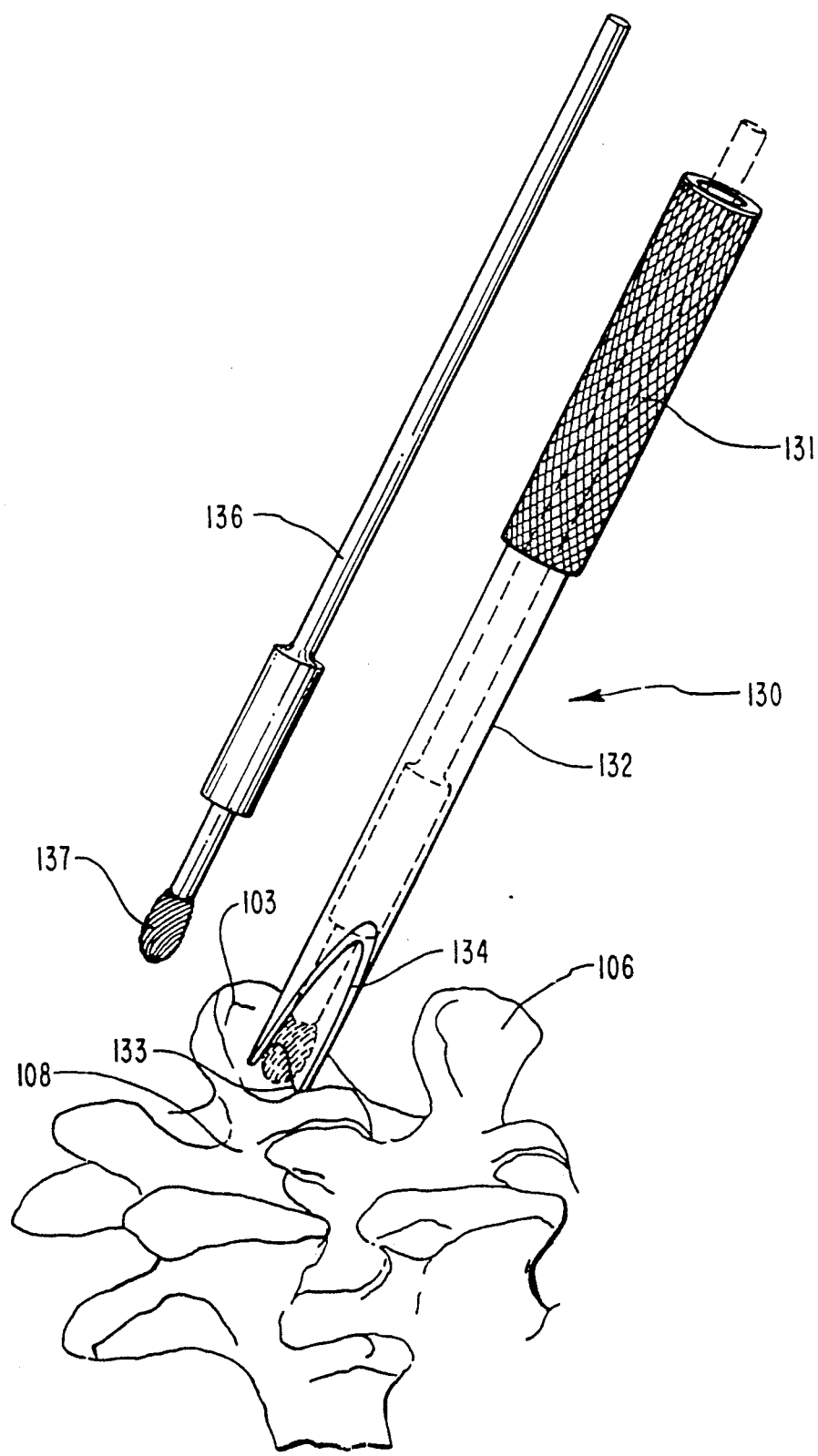
FIG. 14 is a perspective view of a burr and burr guide used for preparing the insertion site for the pedicle screw into the pedicle.

Referring now to FIG. 14, the novel burr guide of this invention is shown generally at 130 and includes a tubular burr guide 132 and a drill burr 136. Burr guide 132 is configured with a knurled hand grip 131 at a proximal end and a pair of opposed cutouts 133 and 134 at the distal end. Cutout 133 is designed to straddle the saddle in the vertebra between the spinous process 103 and the transverse process 106 immediately above the pedicle 108. Cutout 133 thereby securely holds burr guide 132 in position while the surgeon (not shown) selectively orients the axis of burr guide 130 coaxially with pedicle 108. This alignment is achieved by hand grasping knurled hand grip 131 and visually orienting burr guide 130 into the proper alignment. Thereafter, drill burr 136 is telescopically inserted into burr guide 132 as shown by dashed lines until burr 137 on the end thereof contacts the surface of the bone of the transverse process straddled by cutout 133. A drill motor (not shown) is mounted to drill burr 136 and operated to enable burr 137 to cut away the overlying cortical bone to expose the underlying cancellous bone. Drill burr 136 and burr guide 132 are then removed to allow the surgeon (not shown) to use a probe (not shown) to prepare a pilot hole for pedicle screw 20 (FIG. 6A) inserted into pedicle 108.

Sacral Screw Guide

Figure 15:
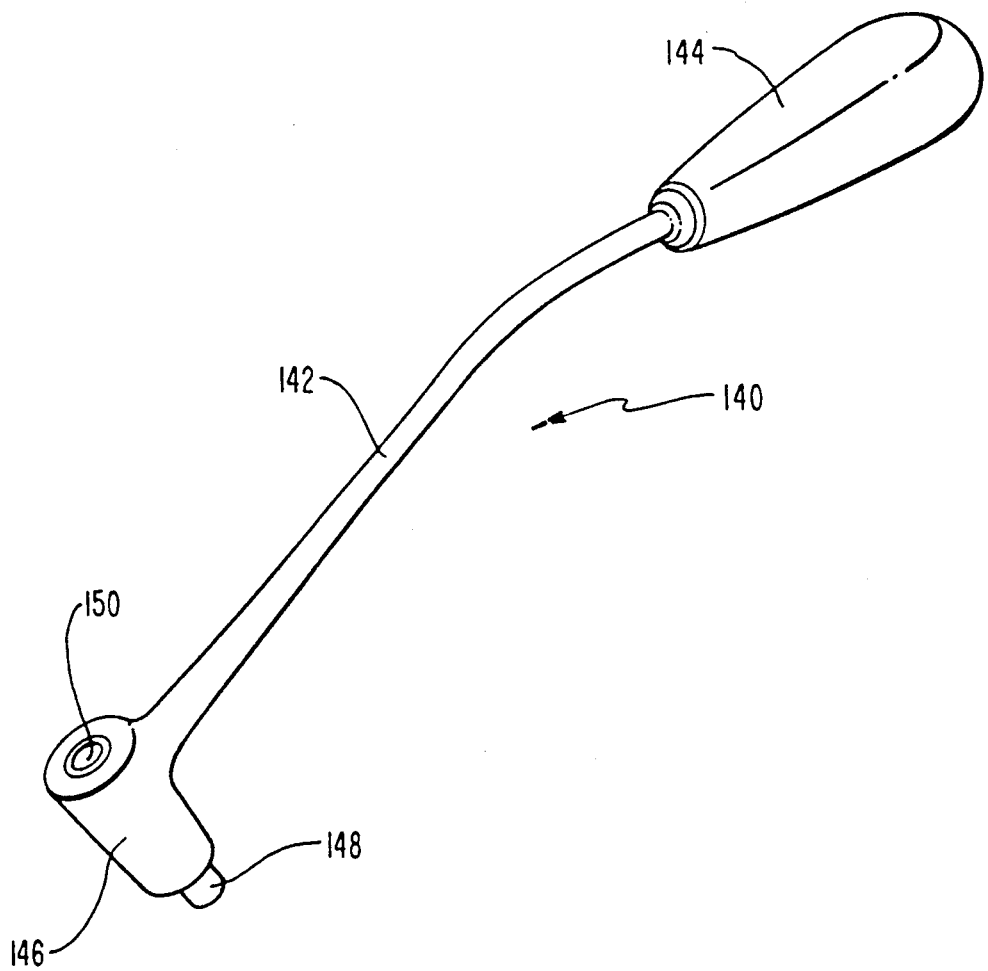
FIG. 15 is a perspective view of a sacral drill guide for preparing the pilot hole into the sacrum for a bone screw.

Referring now to FIG. 15, the novel sacral screw guide of this invention is shown generally at 140 and includes a shaft 142 extending from a handle 144 to a guide body 146. Shaft 112 includes a curvilinear shape to render sacral screw guide 140 ergonomically more useful. Guide body 146 includes a probe 148 and an axial throughbore 150 extending through guide body 146 as well as probe 148. Throughbore 150 functions as a guide for a drill bit (not shown) used to drill the guide holes (not shown) for bone screws 36d and 36e (FIG. 1) to thereby readily assist the surgeon (not shown) in the accurate angular placement of sacral screws 36d and 36e relative to sacrum 106 (FIG. 1).

Referring now also to FIGS. 2A-2D, 3 and 4, probe 148 and the leading end of guide body 146 are each configured to be received, respectively, in threaded ports 34a-34e and countersink 35a-35e in a snug, nesting relationship. Accordingly, the surgeon (not shown) is able to use sacral screw guide 140 in conjunction with sacral rods 30a-30c to accurately achieve alignment of bone screws 36a-36c into the proper engagement in sacrum 106 (FIGS. 1 and 16) to thereby implant bone screws 36a-36e into the greatest bone mass of sacrum 106.

The Method

Referring to all of the figures, the novel spinal fixation apparatus 10 provides the surgeon (not shown) with a versatile method for creating an environment that is highly conducive to the formation of bone ingrowth to create a successful spinal fusion. This important advantage is achieved by providing the surgeon with various interchangeable components that are readily interconnected into spinal fixation apparatus 10. For example, three types of sacral rods, sacral rods 30a-30c, are provided along with three types of bone screws, bone screws 36a-36e, to enable the surgeon to firmly secure the particular sacral rod to sacrum 106. Importantly, each of bone screws 36a-36e is specifically configured to threadedly interlock with the corresponding sacral rod 30a-30c thereby virtually eliminating micromotion between the two components.

Pedicle screw 20 is also a vital component of spinal fixation apparatus 10 because it allows the surgeon to securely affix any one of a longitudinal rod 12 or spinous process hook 14 to either the vertebral body, the pedicle, or the sacrum, depending upon the particular requirements of the surgical procedure. Pedicle screw is unique in that it is relatively simple to implant into the desired bone structure and yet provides a very solid securement.

In practicing the method of this invention, the surgeon (not shown) follows conventional surgical procedures to expose the affected portion of spine 100 and there implant the desired components of spinal fixation apparatus 10. Sacrum 106 provides the primary anchor point for spinal fixation apparatus 10 with sacral rods 30a-30c and/or pedicle screw 20 providing the mechanism by which this anchoring is achieved. Once the specific type of sacral rod 30a-30c has been selected, the surgeon uses sacral screw guide 140 to, first, align sacral rod 30a-30c relative to sacrum 106 particularly with respect to the placement of bone screws 36a-36e relative thereto and, second, drill a pilot hole (not shown) in sacrum 106 using a conventional bone drill (not shown) guided by sacral screw guide 140. The secure mounting of sacral rod 30a-30c to sacrum 106 is easily achieved thereafter by inserting a bone screw 30a-36e into the resulting pilot hole while simultaneously threadedly engaging sacral rods 30a-30c thereby providing secure engagement by bone screws 36a-36e to both sacrum 106 and sacral rods 30a-30c. Importantly, the foregoing threaded engagement between bone screws 36a-36e and sacral rods 30a-30c coupled with the secure embedment of bone screws 36a-36e into sacrum 106 virtually eliminates micromotion between sacral rods 30a-30c and sacrum 106.

The balance of spinal fixation apparatus 10 benefits enormously from this "solid" foundation since it is the fixation of a particular vertebra relative to sacrum 106 that is the primary goal of most posterior spinal surgical procedures. Thus anchored, sacral rods 30a-30c along with pedicle screws 20 are used as the attachment sites for various longitudinal rods 12, spinous process hook 14, universal interlinks 40, 50, and 60 as well as sublaminar hooks 80. Longitudinal rods 12 are also readily adaptable as lateral rods (not shown) transversely across spine 100 and are adapted by being selectively bent into a predetermined curvilinear configuration to assist the surgeon in applying the desired corrective alignment to spine 100. An almost infinite number of orientations among the various element of spinal fixation apparatus 10 are made possible through the use of the highly adaptable, universal interlinks 40, 50, and 60 along with pedicle screw 20 taken in conjunction with the fact that longitudinal rods 12 can be selectively bent to achieve a predetermined curvilinear configuration.

Placement of pedicle screw 20 into pedicle 108 is assisted by the use of burr guide 130 which both orients the axis of drill burr 136 and also holds burr 137 in position against the cortical bone overlying pedicle 108. In this manner, the surgeon is able to easily and accurately abrade away the overlying cortical bone above pedicle 108 to expose the cancellous bone therein. Thereafter, it is a simple matter for the surgeon to carefully prepare a pilot hole downwardly through the cancellous bone using an ordinary probe (not shown). Removal of the probe allows the surgeon to insert and firmly embed pedicle screw 20 through pedicle 108 and into the underlying vertebral body 112, 113, or 114 as the case may be. Shoulder 19 of pedicle screw 20 is seated into the recess created by burr 137 in the cancellous bone thereby providing an additional and, important degree of stability to pedicle screw 20.

While only a few of the various elements of spine fixation apparatus 10 are shown herein for sake of simplicity, it is to be clearly understood that any predetermined number of elements can be configured into the novel spine fixation apparatus 10 of this invention. The only limiting factors in this regard are, of course, the inherent limits of spine 100 to the attachment of these elements to spine 100 as well as any limitations or requirements imposed on the use of spinal fixation apparatus 10 as determined by the nature of the injury, deformity, etc., to spine 100.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A spinal fixation apparatus comprising:
   a rod;
   a plurality of pedicle screws, each pedicle screw comprising an anchor head with a top at one end and a screw shaft extending from the other end of said anchor head, said screw shaft having a predetermined length sufficient to pass through a pedicle of a vertebra and into threaded engagement with a vertebral body of the vertebra, said anchor head comprising a bolt head external profile and a throughbore passing transversely through an axis of said anchor head, said anchor head having a coaxial, blind bore in said top, said pedicle screw including an anchor body configured to be telescopically received in said blind bore, said anchor body having a transverse hole therethrough, said hole being configured to be placed in registry with said throughbore to allow said rod to be passed through said anchor head, said anchor body including a threaded boss and a nut threadedly engaged to said threaded boss and operable to force said anchor body upwardly relative to said anchor head thereby clamping said rod to said anchor head; and a first pedicle screw configured to be embedded in a first vertebra and a second pedicle screw configured to be embedded in a second vertebra with said rod clamped by said first pedicle screw and said second pedicle screw, said rod being configured to rigidly orient the first vertebra to the second vertebra.

2. The spinal fixation apparatus defined in claim 1 wherein said rod comprises a sacral rod, said sacral rod comprising a sacral body and a longitudinal rod extending coaxially from one end of said sacral body, said sacral body comprising a diametrically enlarged cylindrical body having at least one transverse throughbore therethrough, said transverse throughbore being formed in a countersink in said cylindrical body and threadedly receiving a bone screw therethrough.

3. The spinal fixation apparatus defined in claim 2 wherein said bone screw comprises a first thread means for threadedly engaging said transverse throughbore and a second thread means for threadedly engaging bone of a sacrum.

4. The spinal fixation apparatus defined in claim 3 wherein said first thread means and said second thread means are identical and comprise a machine thread.

5. The spinal fixation apparatus defined in claim 2 wherein said sacral body comprises two transverse throughbores therethrough, said transverse throughbores each having an axis angularly offset from said axis of said sacral body.

6. The spinal fixation apparatus defined in claim 5 wherein said axis of said transverse throughbores are angularly offset from each other.

7. The spinal fixation apparatus defined in claim 2 wherein said sacral rod comprises a sacral kit for aligning said sacral body with the sacrum, said sacral kit including a sacral screw guide means comprising a sacral screw guide body and a handle extending outwardly from said sacral screw guide body, said sacral screw guide body having an axial throughbore and a coaxial insert, said insert being received in said transverse throughbore while said sacral screw guide body is partially received in said countersink.

8. The spinal fixation apparatus defined in claim 1 comprising an universal interlink means for clamping a first rod to a second rod.

9. The spinal fixation apparatus defined in claim 8 wherein said universal interlink means comprises a first universal interlink comprising a first clamp, a cleat, a threaded anchor bolt, and a nut threadedly engaged to said threaded anchor bolt, said clamp comprising a clamp body having two planar elements with a first hole extending perpendicularly through said planar elements and a second hole extending transversely through said planar elements and offset from said first hole, said planar elements being separated by a slot, said slot extending into said second hole and enabling said planar elements to close said slot incrementally to clamp a first rod in said second hole, said cleat comprising a yoke for said anchor bolt, said anchor bolt having a transverse hole therethrough, said anchor bolt clamping a second rod between said anchor bolt and said cleat, said nut simultaneously clamping said first rod and said second rod with said first universal interlink.

10. The spinal fixation apparatus defined in claim 8 wherein said universal interlink means comprises a second universal interlink comprising a first clamp body and a second clamp body releasably mountable by a bolt to said first clamp body.

11. The spinal fixation apparatus defined in claim 1 wherein said pedicle screw comprises a pedicle screw stabilizer comprising a housing configured to be telescopically placed downwardly over said anchor head and clamped thereto by said nut, said housing comprising a plurality of prongs for piercingly engaging bone in which said pedicle screw is mounted.

12. The spinal fixation apparatus defined in claim 1 comprising at least one spinous process hook for engaging a spinous process of a vertebra and a sublaminar hook means for engaging a sublaminar of the vertebra, said sublaminar hook means comprising a sublaminar hook comprising a rod clamping means and a downwardly depending hook.

13. The spinal fixation apparatus defined in claim 1 wherein said pedicle screw includes a second anchor head having a rod arm extending perpendicularly from said second anchor head, said rod arm being configurated to be clamped by said pedicle screw.

14. The spinal fixation apparatus defined in claim 1 which further comprises a kit to facilitate the insertion of said pedicle screw, said kit comprising a burr and a burr guide for accurately positioning an opening for a pilot hole through the pedicle, said burr comprising a rotatable shaft having a cutting burr on the end thereof and a drill collar behind said cutting burr, said burr guide comprising a hollow tubular element having a pair of opposing cutouts at one end, said cutouts being configured to straddle the transverse process above the pedicle thereby holding said burr guide in position on the pedicle, said drill collar coaxially orienting said burr in said burr guide while said cutting burr is used to cut away cortical bone from the pedicle.

15. A spinal fixation apparatus kit comprising:
a pedicle screw comprising an anchor head and a distal screw extending from said anchor head, said distal screw having a predetermined length, said predetermined length being sufficient to pass through the pedicle of a vertebra into the vertebral body of the vertebra, said anchor head comprising a blind bore coaxial with said screw and a transverse, rod-receiving hole passing through said anchor head and said blind bore on a diameter of said blind bore, an anchor body telescopically received in said blind bore, said anchor body comprising a transverse throughbore in adjustable alignment with said hole in said anchor head, said anchor body including a threaded bolt coaxial with said screw and a nut threadedly mounted to said threaded bolt, said nut being operable to be tightened against said anchor head thereby pulling said throughbore of said anchor body out of alignment with said hole in said anchor head thereby securely clamping a rod to said anchor head, said pedicle screw further comprising a tapered shoulder between said anchor head and said screw, said tapered shoulder outwardly compressing bone of the vertebra thereby reducing micromotion between said anchor head portion of said pedicle screw and the vertebra, said anchor head comprising an external profile of a bolt head;

a universal interlink comprising a pair of clamps, each of said clamps comprising a body with upper and lower faces oriented in parallel and a throughbore through said faces, a side extension having an outwardly opening, transverse slot, said transverse slot terminating inwardly in a transverse throughbore through said side extension, said transverse throughbore telescopically receiving a rod in a slid fit relationship, said clamp being mountable in a face-to-face relationship with a bolt passing through said throughbore, tightening said bolt causing said transverse slots to become more narrow thereby constricting said transverse throughbores while simultaneously interlocking said pair of clamps;

a sacral rod comprising a mounting body having an axis and a fixation rod extending coaxially from one end of said mounting body, said mounting body comprising at least one mounting hole comprising a countersink and a threaded hole in the bottom of said countersink, said mounting hole having an axis that is angularly offset from said mounting body axis;

a sacral screw for securing said sacral rod to a sacrum comprising a screw and a bolt head with a threaded shoulder between said screw and said bolt head, said threaded shoulder threadedly engaging said threaded hole in said mounting body with said bolt head being received in said countersink; and a rod, said rod having the same diameter as said fixation rod, said rod being conformable and selectively engageable by said universal interlink and pedicle screw, said rod being adaptable to being selectively used as a lateral rod and a longitudinal rod for said spinal fixation apparatus.

16. The spinal fixation apparatus kit defined in claim 15 wherein said pedicle screw comprises a pedicle screw kit for aligning said pedicle screw with the pedicle, said kit comprising a hollow cylindrical burr guide having a notched tip at a first end, said notched tip straddling the transverse process at the pedicle to guide a burr in creating a hole in the cortical bone of the vertebra.

17. The spinal fixation kit apparatus defined in claim 15 wherein said pedicle screw comprises a stabilizer, said stabilizer comprising a hollow housing configured to telescopically engage said anchor, said stabilizer including a plurality of spikes for penetrating the vertebra when said housing is placed downwardly on said pedicle screw.

18. The spinal fixation apparatus kit defined in claim 15 further including a sublaminar hook adjustably mountable to said rod, said sublaminar hook comprising a hook body and a threaded boss extending upwardly from said hook body, a rod clamp, and a threaded nut, said rod clamp having a throughbore therethrough for receiving said threaded boss, said rod clamp engaging said rod when said threaded nut is tightened on said threaded boss, said hook engaging a sublaminar of the vertebrae.

19. The spinal fixation apparatus kit defined in claim 15 wherein said mounting body of said sacral rod comprises a first countersink having a first mounting hole in the bottom of said first countersink and a second countersink having a second mounting hole in the bottom of said second countersink, the axis of said first mounting hole being angularly offset from the axis of said sacral rod and the axis of said second mounting hole being angularly offset from both of said axis of said first mounting hole and said axis of said sacral rod.

20. The spinal fixation apparatus kit defined in claim 19 wherein said sacral rod includes a sacral screw kit having a drill guide means for orienting said sacral screws relative to said axis of said first mounting hole and said axis of said second mounting hole, said drill guide means comprising a cylindrical body having an axial throughbore and terminating at a distal end in a cylindrical guide, the external diameter of said cylindrical body corresponding to the internal diameter of said countersink and the external diameter of said cylindrical guide corresponding to the internal diameter of said mounting hole to thereby guide a drill bit in preparing a hole to receive said sacral screw.

21. A method for providing fixation to a spine comprising the steps of:

obtaining a pedicle screw, said pedicle screw comprising a screw shaft and an anchor head mounted to said screw shaft, said anchor head including a blind bore coaxial with said screw shaft and an anchor body telescopically received in said blind bore, said anchor body including a threaded boss and a nut threadedly engageable to said threaded boss, said anchor head and said anchor body including a throughbore oriented transversely through said anchor head and said anchor body, said throughbore receiving a rod with said nut causing said anchor body to clamp said rod to said anchor head;

mounting at least two of said pedicle screws selectively to vertebrae and the sacrum of the spine;

affixing a rod to the spine by interconnecting said pedicle screws with said rod by passing a portion of said rod into said throughbore; and clamping said rod to said pedicle screws by tightening said nut on said threaded boss on each of said pedicle screws.

22. The method defined in claim 21 wherein said mounting step includes preparing a sacral rod and affixing said sacral rod to the sacrum of the spine while engaging said sacral rod with said pedicle screw to thereby stabilize the relative position of the vertebra to the sacrum.

23. The method defined in claim 22 wherein said affixing step comprises attaching said sacral rod to the sacrum using at least one bone screw, said bone screw being threadedly engaged to said sacral rod and the sacrum.

24. The method defined in claim 23 wherein said attaching step comprises using at least two bone screws, each bone screw being angularly offset from the axis of said sacral rod and from the axis of the other bone screw.

25. The method defined in claim 21 wherein said clamping step includes obtaining a sublaminar hook and a spinous process hook and engaging a portion of a vertebra between said sublaminar hook and said spinous process hook while affixing the relative positions of said sublaminar hook and said spinous process hook on said rod.

26. The method defined in claim 21 wherein said clamping step includes mounting a plurality of pedicle screws on preselected vertebrae and obtaining universal interlinks and a plurality of rods, said universal interlinks adapting said rods to be secured to said pedicle screws.

27. The method defined in claim 21 wherein said mounting step includes preparing the pedicle of the vertebra by cutting away cortical bone of the transverse process above the pedicle with a burr and guiding said burr with a burr guide thereby assuring accurate cutting of the cortical bone.

* * * * *